(12) United States Patent
Osada et al.

(10) Patent No.: US 7,038,171 B2
(45) Date of Patent: May 2, 2006

(54) HOUSEHOLD ELECTRIC APPLIANCES

(75) Inventors: Hideharu Osada, Nara (JP); Hironobu Shibamoto, Osaka (JP); Shoma Osada, Ikoma (JP)

(73) Assignees: Osada Giken Co., Ltd., Osaka (JP); Hideharu Osada, Nara (JP)

( * ) Notice: Subject to any disclaimer, the term of this patent is extended or adjusted under 35 U.S.C. 154(b) by 0 days.

(21) Appl. No.: 10/980,161

(22) Filed: Nov. 4, 2004

(65) Prior Publication Data
US 2005/0109751 A1 May 26, 2005

(30) Foreign Application Priority Data
Nov. 10, 2003 (JP) .............................. 2003-379432

(51) Int. Cl.
*A61L 9/16* (2006.01)
*A61L 9/00* (2006.01)
*B01D 50/00* (2006.01)

(52) U.S. Cl. ............... 219/385; 219/386; 219/201; 219/209; 219/221; 392/360; 392/383; 392/385; 422/4; 422/120; 422/122

(58) Field of Classification Search ........ 219/385–387, 219/391, 393, 396, 400, 402, 411, 200, 209, 219/221; 392/386, 407
See application file for complete search history.

(56) References Cited

U.S. PATENT DOCUMENTS

| 2,900,290 | A | * | 8/1959 | Bethge | 219/528 |
|---|---|---|---|---|---|
| 5,002,826 | A | * | 3/1991 | Pollart et al. | 428/323 |
| 5,195,165 | A | * | 3/1993 | Ono et al. | 392/407 |
| 5,388,177 | A | * | 2/1995 | Ono et al. | 392/386 |
| 5,756,215 | A | * | 5/1998 | Sawamura et al. | 428/446 |
| 5,891,402 | A | * | 4/1999 | Sassa et al. | 422/122 |
| 6,034,354 | A | * | 3/2000 | Hironaka | 219/383 |
| 6,100,503 | A | * | 8/2000 | Sasaki et al. | 219/411 |
| 6,125,234 | A | * | 9/2000 | de Jenlis | 392/439 |
| 6,448,540 | B1 | * | 9/2002 | Braunisch et al. | 219/685 |
| 2003/0006230 | A1 | * | 1/2003 | Kaji et al. | 219/620 |
| 2004/0241040 | A1 | * | 12/2004 | Wei et al. | 422/4 |
| 2005/0089451 | A1 | * | 4/2005 | Huang | 422/121 |

FOREIGN PATENT DOCUMENTS

| JP | 03241264 A | * | 10/1991 |
|---|---|---|---|
| JP | 11-169725 A | * | 6/1999 |
| JP | 11-197514 A | * | 7/1999 |
| JP | 2000126029 A | * | 5/2000 |
| JP | 2000225321 A | * | 8/2000 |
| JP | 2000273392 A | * | 10/2000 |

\* cited by examiner

*Primary Examiner*—Joseph Pellham
(74) *Attorney, Agent, or Firm*—Armstrong, Kratz, Quintos, Hanson & Brooks, LLP

(57) ABSTRACT

A household electric appliance including a heating part and titanium oxide particles to be activated by heating, the heating part being a heating device inherently possessed by the household electric appliance and/or an additional heating device not inherently possessed by the household electric appliance.

6 Claims, 1 Drawing Sheet

HOUSEHOLD ELECTRIC APPLIANCES

BACKGROUND OF THE INVENTION

1. Field of the Invention

The present invention relates to household electric appliances.

2. Prior Art

There exist various household electric appliances which applied to various usages. Some among them, such as electric grill, oven, toaster, etc. generates malodor, bad smell or not-preferable components inevitably from their specific usages. The malodor not only makes people uncomfortable but also is harmful to them. Besides, the appliances themselves are often polluted.

The household electric appliances are often or happen to be made use of in an environment having existence of malodor and pollution in itself.

It is very much favorable if the household electric appliances can serve to remove the malodor and the polluting substances in a simple manner. But, almost of them do not have such function.

Hence, a household electric appliance mitigating at maximum the problems is provided here.

SUMMARY OF THE INVENTION

Under the above circumstances, the inventor studied zealously and accomplished the household electric appliances according to the present invention which is characterized in including and having "a heating part" and "titanium oxide particles activated by heating".

DETAILED DESCRIPTION OF THE INVENTION

Figure 1:
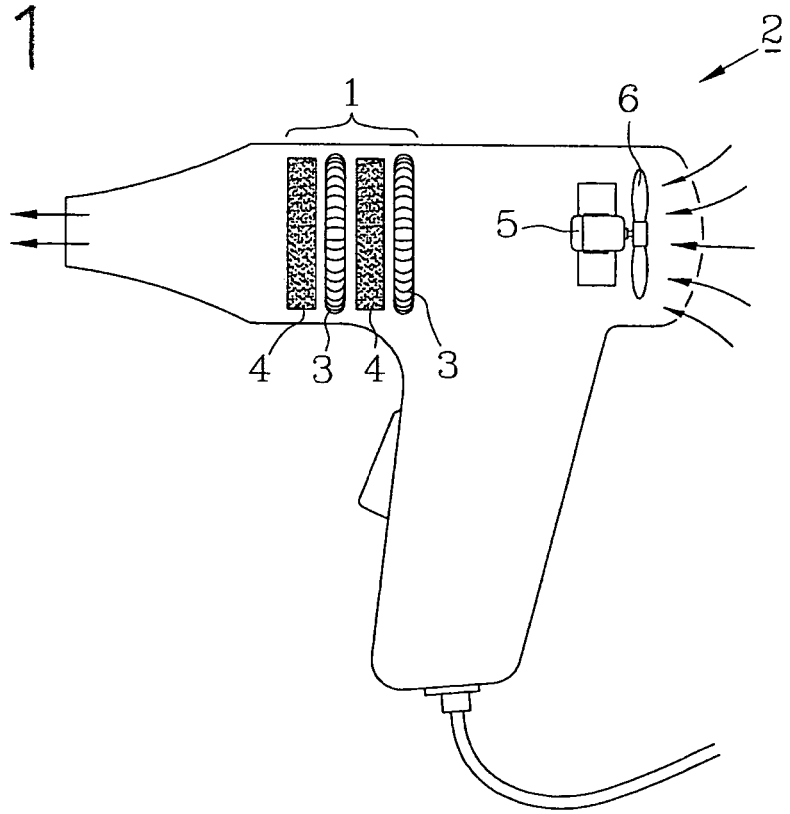
FIG. 1 is a schematic sectional view showing an example of a hair drier 1 which is one of the household electric appliances according to the present invention.

The household electric appliances referred to herein are those used domestically and making use of electricity. Electricity may be in style of being additional or accessory, or in type of batteries.

The household electric appliances may be a household drying apparatus, a floor heating system, an electric carpet, a legless chair for use on Japanese "tatami" mat, an electric "kotatsu" heater, an electric stove, a bathroom heating system, an electric blanket, a heating type humidifier, an oil fan-heater, an IH cooking heater, an electric rice cooker, an electric pot, an electric oven-range, a toaster, a heating apparatus, a household baking machine, a coffee maker, a gas grill, a gas table, an infrared rays stove, or an oil far infrared rays heater, or a cleaning device, an electric clock, a television set, or a radio each not having a means for the purpose of heating, or (without being limited to those) may include all of the household electric appliances to be used in the house.

The household electric appliances further may be any devices such as an air cleaning apparatus, a deodorizing apparatus or the like whose main purpose is decomposition of components of malodor and polluting substances, the Purpose of the present invention.

The "heating part" referred to in the present application is a part directly having an increase of temperatures and may be a part of the household electric appliance inherently possessed by the electric appliance or additionally provided thereto or may be provided by both of the ways.

The heating part inherently possessed by the specific electric appliance may include those provided for heating (such as a heater in a toaster, a gas burner in a grill) and those directly having a temperature rise not for the purpose of heating (such as an electric motor).

Any heating part which not provided inherently on the electric appliances is, for example, the heating part provided on a cleaner. The cleaners do not at all need (and therefore not possess inherently) a heater in view of their function. However, the present invention may provide a heating device, for example, on such cleaners irrespective of the inherent function and purpose of the cleaners.

A style of heating may be electric (such as by electrically heated wire itself (a covering may be provided thereon), a lamp, high frequency, ultrasonic wave, magnetic induction, heat insulating compression, or other systems each generating heat )or by burning fuels (such as burning gas, kerosine, or the like).

Titanium oxide particles are known well as a photocatalyst and are activated by heat so as to be for use in the present invention. Oxide titanium is preferably anatase crystal or may use other crystal structures. Moreover, the crystal may contain mixed other atoms (e.g. N). Size of the particles may be the same as that of commercially available titanium oxide photo-catalyst, namely, several nm to several μm. Alternatively, the particles may be subjected to granulation process to be made larger in size, preferably, to the extent of 0.01 mm to several mm.

Further, the titanium oxide particles may be mixed with many kinds of metal particles, for example, rare earth elements such as yttrium, lanthanum etc, platinum, niobium, vanadium or the like.

The titanium oxide particles (including metal) held by or carried on various carriers may be usable. Also usable are the titanium oxide particles many of which themselves are adhered or fixed to one another by use of an adhesive to be made larger in size. The carriers may employ quartz sand (silica sand), balloons or the like. The adhesive for adhering or fixing titanium oxide particles to the carriers or for adhering titanium oxide particles themselves to one another may employ silicon or the like which is not likely to be decomposed, inorganic substances such as cement or the like, or titanium alcoxide or the like.

The present invention causes that titanium oxide is heated by the "heating part" whereby to be excited and activated and oxidize and decompose substances placed thereabouts. As seen, the base of the present invention is the fact that titanium oxide (preferably the photo-catalyst type) is activated by heating only.

The extent of heating of titanium oxide may necessitate 50 or 60° C. at minimum depending upon specific devices. For example, a toaster and a hair dryer, as they are, are sufficient for the purpose of the present invention since they could have an increased temperature of several hundreds degrees at their high temperature region. Meanwhile, in case of using heat from a motor or the like, an additional heating means is preferably provided.

Next, explanation will be given on provision of titanium oxide.

It is preferable that titanium oxide is heated and air flows thereabouts and circulates in the device or is discharged to an object. In a cleaner which is adapted to absorb the ambient air, titanium oxide is to be provided at a part where the absorbed ambient air flows through.

Titanium oxide may be conveniently filled, in the form of particles, in a bag or a container having meshes or may be fixed to an unwoven fabric or a porous member, such as a filter. For example, titanium oxide may be provided in a hair dryer in such manner as being filled in a bag having meshes to allow air to sufficiently flow to the air outlet.

Also, a fan may be provided to positively cause ambient air or gas inside the apparatus to contact with titanium oxide, whereby largely improving an efficiency of contact.

An additional heating device may be provided with an exclusively usable switch to be used only for such additional heating device, so that heating is carried out only when needed.

PREFERRED EMBODIMENTS OF THE INVENTION

FIG. 1 is a schematic sectional view showing an example of a hair dryer 1 which is one of the household electric appliances according to the present invention. The hair dryer is provided in the inside with a heater unit 2 comprising an electric heater 3 ("the heating part") and a filter 4 to which titanium oxide particles are applied. Both of the electric heater 3 and the filter 4 are so structured as to fully ensure or achieve air flow. The titanium oxide particles applied filter 4 comprises a thin box-like shaped container made of a metal net of large mesh and filled with titanium oxide particles carried by silica sand. Titanium oxide particles are made larger in size to reduce air resistance. Size of silica sand is about 1 mm. The box-like shaped container may be provided at its middle part with a bore/bores through which air flows.

A fan 6 to be driven by a motor 5 is provided behind the heater unit 2. In detail, this appliance has almost the same structure as the ordinary hair dryer except the part related to titanium oxide. When the hair dryer according to the present invention is used in a usual manner, titanium oxide is heated by the heating part 3 to thereby be activated, so that malodor components and polluting substances when contained in air flowing along the heated and activated titanium oxide are decomposed. The decomposing function acts or is effective to any components to be decomposed when exist outside the hair dryer (at the place in continuation to the air outlet of the hair dryer) but not at the place along the heated and activated titanium oxide inside the hair dryer.

Figure 2:
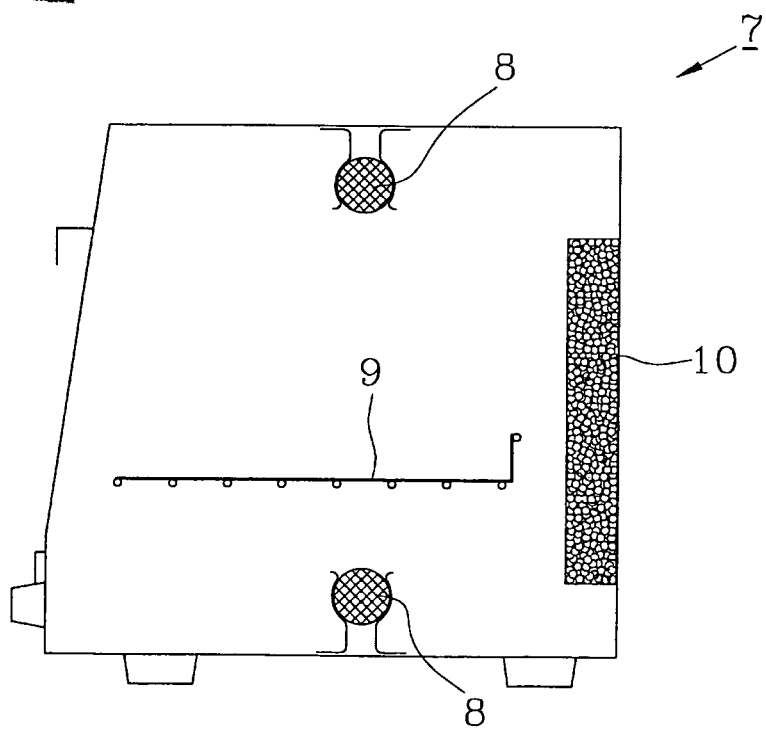
FIG. 2 is a schematic sectional view showing an example of a toaster 7 which is one of the household electric appliances according to the present invention.

FIG. 2 shows an example of an oven toaster 7 comprising two electric heaters 8 in a lamp type aligned vertically with respect to a grill netting 9 at the middle part. A titanium oxide unit 10 is mounted on the rear part of the oven toaster. The titanium oxide unit 10 comprises a net-like shaped container filled with titanium oxide particles. Although there is not provided positive sending of air by use of a fan, oxygen and hydroxide ion activated by convection caused from temperature difference inside the room are fed to every place. Oxidation and decomposing reaction of malodor components and polluting substances occur there. Since organic substances do not stick or adhere directly onto titanium oxide particles, the system is inferred to be able to be usable semi-permanently.

EFFECT OF THE INVENTION

The household electric appliances according to the present invention have the excellent advantages as follows.
(1) Since titanium oxide is heated, organic substances which exist at a place or in a room where air flowing along the heated titanium oxide passes are decomposed or oxidized, thereby decomposing pollution and causing malodor to disappear.
(2) The household electric appliances show excellent effects merely by using the appliances in a usual manner. Hence, there is no need to know existence of titanium oxide upon use of the appliances.
(3) The effects of the present invention lasts or can be maintained semi-permanently.
(4) The present invention can be applied to any usual household electric appliances which has a heating part or is provided with the same.
(5) Even in personal computers which are hard to be given inside cleaning, pollution is decomposed, thereby reducing troubles of cleaning.
(6) In case of having no problems inside any electric appliances, the effect purifying ambient air (air inside the rooms or the like) is obtained. For example, while a user watching television, deodorization is achieved in the room.

What we claimed is:

1. A household electric appliance inherently possessing a heating part, the household electric appliance comprising a titanium oxide unit filled with titanium oxide particles to be activated by heating of the heating part, the titanium oxide unit so setting titanium oxide particles that air can flow through gaps among titanium oxide particles, titanium oxide being anatase type crystal, and the household electric appliance not having any electromagnetic wave applying devices for activating titanium oxide.

2. A household electric appliance as set forth in claim 1 wherein titanium oxide is fixed to a filter.

3. A household electric appliance as set forth in claim 1 wherein titanium oxide employs titanium oxide particles of several nm which are subjected to granulation process to be made larger in size to the extent of 0.01 mm to several mm.

4. A household electric appliance as set forth in claim 3 wherein titanium oxide is filled, in the form of particles, in a bag or a container having meshes.

5. A household electric appliance as set forth in one of claims 1 through 4 wherein titanium oxide particles are mixed with metal particles.

6. A household electric appliance as set forth in one of claims 1 through 4 wherein titanium oxide particles are held and carried by a carrier by use, for the holding and carrying, of an adhesive such as inorganic adhesive or titanium alcoxide.

* * * * *